US008652812B2

(12) United States Patent
Miller

(10) Patent No.: US 8,652,812 B2
(45) Date of Patent: Feb. 18, 2014

(54) DUAL OLIGONUCLEOTIDE METHOD OF NUCLEIC ACID DETECTION

(71) Applicant: 3M Innovative Properties Company, St. Paul, MN (US)

(72) Inventor: Jesse D. Miller, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/681,574

(22) Filed: Nov. 20, 2012

(65) Prior Publication Data

US 2013/0171635 A1 Jul. 4, 2013

Related U.S. Application Data

(63) Continuation of application No. 12/680,049, filed as application No. PCT/US2008/077831 on Sep. 26, 2008, now Pat. No. 8,313,931.

(60) Provisional application No. 60/976,260, filed on Sep. 28, 2007.

(51) Int. Cl.
*C12P 19/34* (2006.01)
*C12Q 1/68* (2006.01)

(52) U.S. Cl.
USPC .................................... 435/91.2; 435/6.1

(58) Field of Classification Search
USPC ................................. 435/91.2, 6.1
See application file for complete search history.

(56) References Cited

U.S. PATENT DOCUMENTS

| | | | |
|---|---|---|---|
| 3,687,808 A | 8/1972 | Merigan, Jr. et al. |
| 4,469,863 A | 9/1984 | Ts'o et al. |
| 4,996,143 A | 2/1991 | Heller et al. |
| 5,035,996 A | 7/1991 | Hartley |
| 5,235,033 A | 8/1993 | Summerton et al. |
| 5,565,322 A | 10/1996 | Heller |
| 5,596,086 A | 1/1997 | Matteucci et al. |
| 5,683,896 A | 11/1997 | Hartley et al. |
| 5,750,666 A | 5/1998 | Caruthers et al. |
| 5,849,489 A | 12/1998 | Heller |
| 5,945,313 A | 8/1999 | Hartley et al. |
| 6,162,603 A | 12/2000 | Heller |
| 6,627,159 B1 | 9/2003 | Bedingham et al. |
| 6,720,187 B2 | 4/2004 | Bedingham et al. |
| 6,734,401 B2 | 5/2004 | Bedingham et al. |
| 6,814,935 B2 | 11/2004 | Harms et al. |
| 6,987,253 B2 | 1/2006 | Bedingham et al. |
| 7,026,168 B2 | 4/2006 | Bedingham et al. |
| 7,164,107 B2 | 1/2007 | Bedingham et al. |
| 7,192,560 B2 | 3/2007 | Parthasarathy et al. |
| 2006/0263816 A1 | 11/2006 | Laikhter et al. |
| 2007/0154940 A1 | 7/2007 | Inose |

FOREIGN PATENT DOCUMENTS

| | | |
|---|---|---|
| CN | 1653191 A | 8/2005 |
| CN | 101033486 A | 9/2007 |
| EP | 0 861 906 | 9/1998 |
| EP | 1 726 664 | 11/2006 |
| EP | 1 780 291 | 5/2007 |
| WO | WO 97/46707 | 12/1997 |
| WO | WO 97/46712 | 12/1997 |
| WO | WO 97/46714 | 12/1997 |
| WO | WO 99/49293 | 9/1999 |
| WO | WO 2006/119326 | 11/2006 |
| WO | WO 2007/060707 | 5/2007 |

OTHER PUBLICATIONS

Guo, Shijun et al.; "Application of FRET in Fluorescence Detection of FQ-PCR"; Chinese Journal of Medical Instrumentation; vol. 31, No. 1; 2007; pp. 39-43.
Hessner, M.J. et a.; "Utilization of labeled tracking oligonucleotide for visualization and quality control of spotted 70-mer arrays"; BMC Genomics; vol. 5, No. 12; 2004; pp. 1-11.
Ahmad, New FRET Primers for Quantitative Real-Time PCR, Anal. Bioanal. Chem., vol. 387, pp. 2737-2743, (2007).
Epstein, Fluorescence-Based Nucleic Acid Detection and Microarrays, Analytica Chimica Acta, vol. 469, pp. 3-36, (2002).
Fiandaca, Self-Reporting PNA/DNA Primers for PCR Analysis, Genome Res., vol. 11, pp. 609-613, (2001).
Hyrup, Peptide Nucleic Acids (PNA): Synthesis, Properties and Potential Applications, Bioorgan. Med. Chem., vol. 4, No. 1, pp. 5-23, (1996).
Li, Antiprimer Quenching-Based Real-Time PCR for Simplex or Multiplex DNA Quantification and Single-Nucleotide Polymorphism Genotyping, Nature Protocols, vol. 2; No. 1, pp. 50-58, (2007).
Notomi, Loop-Mediated Isothermal Amplification of DNA, Nucleic Acids Research, vol. 28, No. 12, E63 pp. i-vii, (2000).
Nuovo, In Situ Amplification Using Universal Energy Transfer-Labeled Primers, J. of Histochem. & Cytochem., vol. 47, No. 3; pp. 273-279, (1999).
SantaLucia, Jr., A Unified View of Polymer, Dumbbell, and Oligonucleotide DNA Nearest-Neighbor Thermodynamics, Proc. Natl. Acad. Sci. USA, vol. 95, pp. 1460-1465, (Feb. 1998).
Santangelo, Nanostructured Probes for RNA Detection in Living Cells, Annals of Biomedical Engineering, vol. 34, No. 1, pp. 39-50, (Jan. 2006).
Solinas, Duplex Scorpion Primers in SNP Analysis and FRET Applications, Nucleic Acids Research, vol. 29, No. 20, E96 pp. 1-9 (2001).
Summerton, Morpholino Antisense Oligomers: Design, Preparation, and Properties, Antisense & Nucleic Acid Drug Development, vol. 7, No. 3, pp. 187-195, (1997).
The Handbook—A Guide to Fluorescent Probes and Labeling Technologies from Molecular Probes (www.probes.invitrogen.com/handbock) Tenth Edition by Richard P. Haugland, Ph.D.; 2005; pp. Title pg, copyright pg, table of contents, Chapter 1 pp. 7-25, Chapter 2 pp. 93-108 (Total pages submitted 41).
Vincent, Helicase-Dependent Isothermal DNA Amplifcation, EMBO Reports, vol. 5, No. 8, pp. 795-800, (2004).
Whitcombe, Detection of PCR Products Using Self-Probing Amplicons and Fluorescence, Nature Biotech., vol. 17, pp. 804-807, (Aug. 1999).
Yi, Molecular Zipper: A Fluorescent Probe for Real-Time Isothermal DNA Amplification, Nucleic Acids Research, vol. 34, No. 11,E81 pp. 1-5, (2006).
Yurke, A DNA-Fuelled Molecular Machine Made of DNA, Nature, vol. 406, pp. 605-608, (Aug. 10, 2000).

*Primary Examiner* — Cynthia B Wilder

(57) ABSTRACT

Methods for amplifying and detecting nucleic acids are described, as well as sets of 5' labeled oligonucleotides.

4 Claims, 3 Drawing Sheets

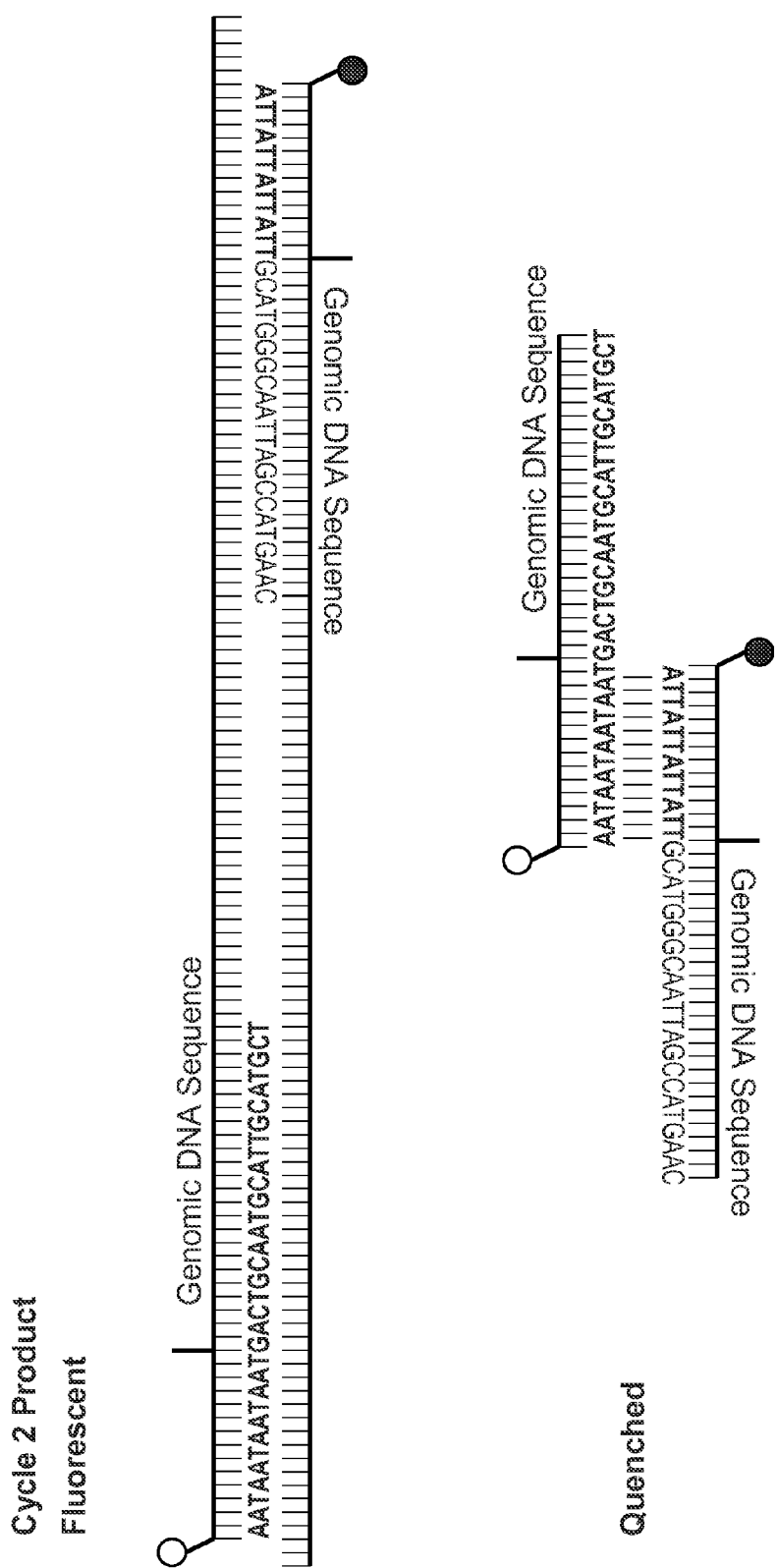

DUAL OLIGONUCLEOTIDE METHOD OF NUCLEIC ACID DETECTION

CROSS REFERENCE TO RELATED APPLICATIONS

This application is a continuation of U.S. application Ser. No. 12/680,049, filed Sep. 26, 2008 (now U.S. Pat. No. 8,313, 931), which was a national stage filing under 35 USC 371 of PCT/US2008/077831 filed Sep. 26, 2008, which International Application was published by the International Bureau in English on Apr. 2, 2009, which application claims the benefit of U.S. Provisional Patent Application No. 60/976, 260, filed Sep. 28, 2007, which is incorporated herein by reference in their entirety.

This application has associated with it a sequence listing with the file name Sequence_Listing_ST25_63553US013.TXT, created Mar. 8, 2013 and contains 2,658 bytes, which is incorporated herein by reference.

BACKGROUND

1. Technical Field

This document relates to methods and materials for detecting nucleic acids. More specifically, this document relates to methods for detecting nucleic acids using two 5' labeled oligonucleotides that contain sequences complementary to each other as well as sequences complementary to different portions of a target nucleic acid.

2. Background Information

The fluorescence resonance energy transfer (FRET) mechanism has been incorporated into a variety of assays for detecting nucleic acids, including molecular beacons and Taqman assays. See Epstein et al. (2002), *Analytica Chimica Acta*, 469:3-36. With molecular beacons, a single stranded probe is used that can form a hairpin structure. The probe is dual labeled, containing a fluorophore on one end and a quencher on the other end. When the probe is in the hairpin conformation, fluorescence is quenched. Upon hybridization to its target, fluorescence is observed. Taqman assays rely on the 5'-exonuclease activity of a DNA polymerase to digest a dual-labeled probe, which physically separates the fluorescent labeled nucleotide from the quencher and results in an increase in fluorescence. A need exists for a method of nucleic acid detection that does not require dual labeled probes or more than two oligonucleotides.

SUMMARY

Disclosed is a simplified method for amplifying and detecting nucleic acids that uses two 5' labeled oligonucleotides that contain 5' complementary sequences and 3' target specific sequences. When the oligonucleotides anneal to their target, fluorescence is observed. In contrast, when the oligonucleotides anneal to each other, fluorescence is quenched. The methods described herein have reduced background relative to traditional real-time amplification techniques and can be used for detecting nucleic acids from a variety of samples.

In one aspect, the invention features a set of oligonucleotides for detecting a target nucleic acid. The set of oligonucleotides includes a first and a second oligonucleotide. The first oligonucleotide includes a 5' and 3' nucleotide sequence, wherein the 5' nucleotide sequence is 5-23 nucleotides in length beginning at the 5' end of the first oligonucleotide, wherein the 3' sequence is at least 80% (e.g., at least 90% or 99%) identical to a first portion of the target nucleic acid, and wherein a fluorescent moiety is attached in the 5' nucleotide sequence (e.g., to the 5' terminal nucleotide) of the first oligonucleotide. The second oligonucleotide includes a 5' and 3' nucleotide sequence, wherein the 5' nucleotide sequence is 5-23 nucleotides in length beginning at the 5' end of the second oligonucleotide, wherein the 3' nucleotide sequence is at least 80% (e.g., at least 90% or 99%) identical to a second portion of the target nucleic acid, and wherein an acceptor moiety is attached in the 5' nucleotide sequence (e.g., to the 5' terminal nucleotide) of the second oligonucleotide. The 5' nucleotide sequence of the first oligonucleotide is at least 80% (e.g., at least 90% or 99%) identical to the complement of the 5' nucleotide sequence of the second oligonucleotide. The 3' nucleotide sequence of each oligonucleotide is not labeled with a fluorescent moiety or an acceptor moiety that is compatible with the fluorescent moiety attached to the first oligonucleotide or the acceptor moiety attached to the second oligonucleotide. The first and second oligonucleotides can be 25 to 50 nucleotides in length.

The 5' nucleotide sequences of the first and second oligonucleotides anneal to each other at a temperature that is lower than the temperature required for annealing of the 3' nucleotide sequence of either of the first or second oligonucleotides to the target nucleic acid. For example, the 5' nucleotide sequences of the first and second oligonucleotides can anneal to each other at a temperature that is lower than the temperature required for annealing of the 3' nucleotide sequence of both the first or second oligonucleotides to the target nucleic acid.

The acceptor molecule can be a quencher (e.g., IOWA BLACK). The oligonucleotides can anneal to each other at 42° C. to 50° C., and the fluorescence of the fluorescent moiety can be quenched at the annealing temperature. Fluorescence can be quenched at least 50% relative to the fluorescence of the fluorescent moiety in the absence of quenching. The maximum emission spectrum of the fluorescent moiety can be between 420 and 620 nm (e.g., 6-carboxyfluorescein (6-FAM), Rhodamine Green, Oregon Green, hexachlorofluorescein (HEX), 6-carboxy-4',5'-dichloro-2',7'-dimethoxyfluorescein (JOE), tetrachlorofluorescein (TET), or indodicarbocyanine 3 (Cy3)).

The set of oligonucleotides further can include third and fourth oligonucleotides for detecting a different target nucleic acid. The third oligonucleotide can include a 5' and 3' nucleotide sequence, wherein the 5' nucleotide sequence is 5-23 nucleotides in length beginning at the 5' end of the third oligonucleotide, wherein the 3' sequence is at least 80% (e.g., at least 90% or 99%) identical to a first portion of the different target nucleic acid, and wherein a fluorescent molecule is attached in the 5' nucleotide sequence (e.g., to the 5' terminal nucleotide) of the third oligonucleotide. The fourth oligonucleotide can include a 5' and 3' nucleotide sequence, wherein the 5' nucleotide sequence is 5-23 nucleotides in length beginning at the 5' end of the fourth oligonucleotide, wherein the 3' nucleotide sequence is at least 80% (e.g., at least 90% or 99%) identical to a second portion of the different nucleic acid, and wherein an acceptor molecule is attached in the 5' nucleotide sequence (e.g., to the 5' terminal nucleotide) of the fourth oligonucleotide. The 5' nucleotide sequence of the third oligonucleotide is at least 80% (e.g., at least 90% or 99%) identical to the complement of the 5' nucleotide sequence of the fourth oligonucleotide. The 3' nucleotide sequence of each of the third and fourth oligonucleotides is not labeled with a fluorescent moiety or an acceptor moiety that is compatible with the fluorescent moiety attached to the first or third oligonucleotide, or the acceptor moiety attached to the second or fourth oligonucleotide.

The invention also features a method for detecting the presence or absence of a target nucleic acid in a biological sample. The method includes (a) contacting the biological sample with a set of oligonucleotides to produce a fluorescently labeled amplicon if the target nucleic acid is present in the sample and (b) detecting fluorescence of the amplicon. The set of oligonucleotides includes two oligonucleotides as described herein. The contacting and detecting steps can take place under real-time PCR conditions. The detecting step can include quantitating the amount of fluorescence. The amplicon can be between 30 and 500 (e.g., 50 to 150) nucleotides in length.

In another aspect, the invention features a method for detecting the presence or absence of at least two target nucleic acids in a biological sample. The method includes (a) contacting the biological sample with a set of oligonucleotides to produce two fluorescently labeled amplicons if the target nucleic acids are present in the sample; and (b) detecting fluorescence of the amplicons. The set of oligonucleotides includes four oligonucleotides as described herein.

In yet another aspect, the invention features a kit for detecting a nucleic acid. The kit includes a set of oligonucleotides as described herein. The kit further can include a DNA polymerase, $MgCl_2$, KCl, or deoxyribonucleotide triphosphates (dNTPs).

The invention also features a reaction mixture for fluorescence-based monitoring of a polymerase chain reaction. The reaction mixture includes a set of oligonucleotides as described herein, a DNA polymerase, dNTPs, and $MgCl_2$. The reaction mixture further can include a fluorescently labeled amplicon. The 5' nucleotide sequence of the sense strand of the amplicon has at least 80% sequence identity to the complement of the 5' nucleotide sequence of the antisense strand of the amplicon, wherein the 5' nucleotide sequences are 5 to 23 nucleotides in length beginning at the 5' end of each strand of the amplicon, and wherein the 5' nucleotide sequence of one strand of the amplicon is labeled with a fluorescent moiety and the 5' nucleotide sequence of the other strand of the amplicon is labeled with a compatible acceptor moiety. The amplicon can be 30 to 500 nucleotides in length.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWING

FIG. 1A-1C is a schematic of the amplification procedure using a pair of 5' labeled primers.

DETAILED DESCRIPTION

Figure 1A:
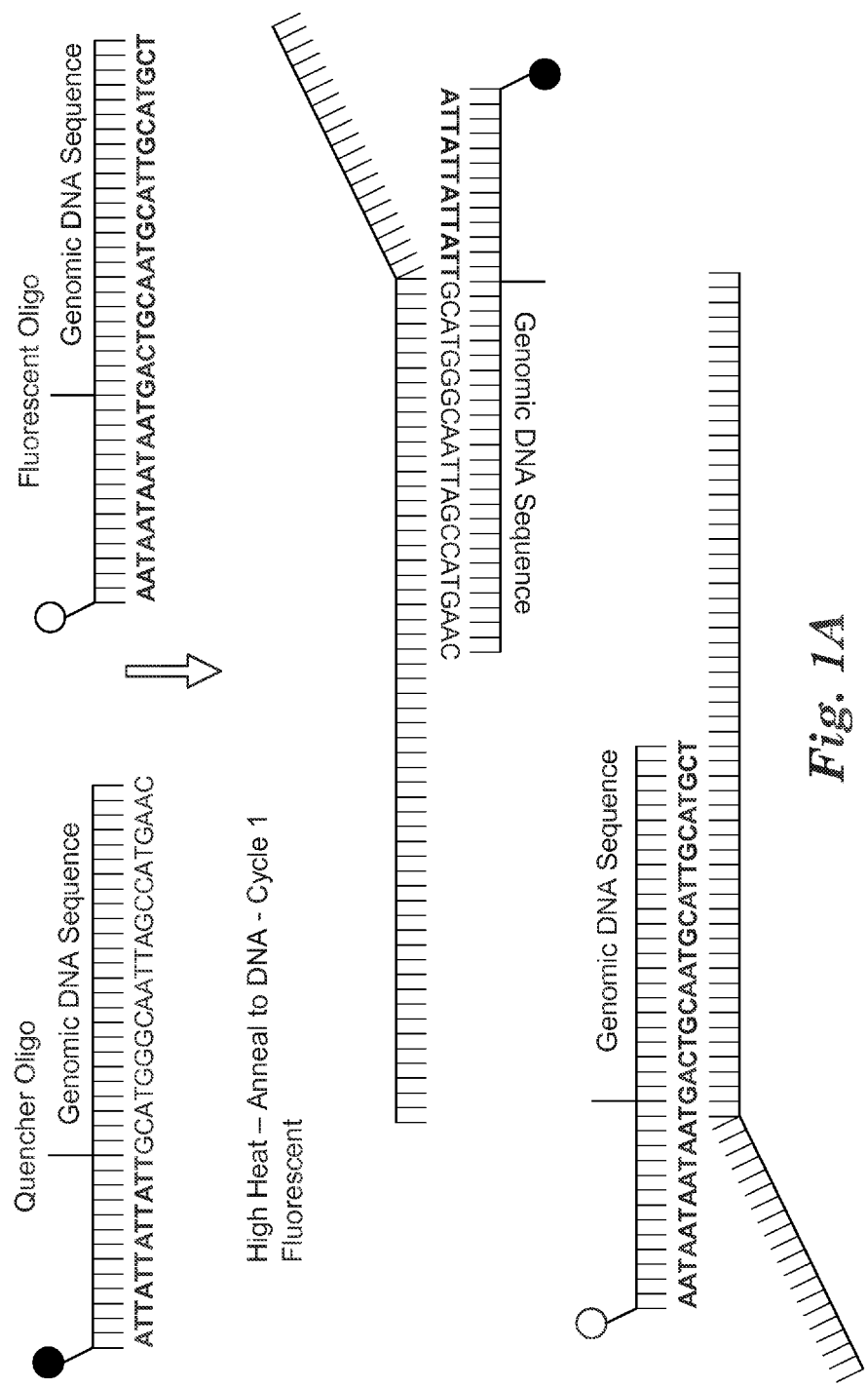

In general, materials and methods are disclosed for amplifying and detecting nucleic acids using a set of two oligonucleotides, where the 5' nucleotide sequences of the oligonucleotides are complementary to each other, and the 3' nucleotide sequences are complementary to different portions of a target specific sequence. Each oligonucleotide is labeled in the 5' nucleotide sequence (e.g., at the 5' terminus (end) thereof); one oligonucleotide is labeled with a fluorescent donor moiety and the other oligonucleotide is labeled with a compatible acceptor moiety. As described below, such pairs of oligonucleotides can be used as primers for amplifying and detecting nucleic acids in real time, without the need for dual labeling or additional oligonucleotide primers or probes.

Oligonucleotides

As used herein, the term "oligonucleotide" refers to an oligomer or polymer of ribonucleic acid (RNA) or deoxyribonucleic acid (DNA), or analogs thereof. Nucleic acid analogs can be modified at the base moiety, sugar moiety, or phosphate backbone to improve, for example, stability, hybridization, or solubility of a nucleic acid. Modifications at the base moiety include substitution of deoxyuridine for deoxythymidine, and 5-methyl-2'-deoxycytidine and 5-bromo-2'-deoxycytidine for deoxycytidine. Other examples of nucleobases that can be substituted for a natural base include 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Other useful nucleobases include those disclosed, for example, in U.S. Pat. No. 3,687,808.

Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone (e.g., an aminoethylglycine backbone) and the four bases are retained. See, for example, Summerton and Weller (1997) *Antisense Nucleic Acid Drug Dev.* 7:187-195; and Hyrup et al. (1996) *Bioorgan. Med. Chem.* 4:5-23. In addition, the deoxyphosphate backbone can be replaced with, for example, a phosphorothioate or phosphorodithioate backbone, a phosphoramidite, or an alkyl phosphotriester backbone. See, for example, U.S. Pat. Nos. 4,469,863, 5,235,033, 5,750,666, and 5,596,086 for methods of preparing oligonucleotides with modified backbones.

Oligonucleotides of the invention can be between 15 and 50 (e.g., 15-30, 25-50, 30-45, 33-40, 20, 21, 22, 23, 24, 25, 26, 27, 28, 29, 30, 31, 32, 33, 34, 35, 35, 37, 38, 39, or 40) nucleotides in length and have 5' nucleotide sequences that are complementary to each other. Typically, the 5' nucleotide sequences are 5 to 23 nucleotides in length beginning at the 5' end of the oligonucleotide. It is understood in the art that the sequence of an oligonucleotide need not be 100% complementary to that of its target nucleic acid in order for hybridization to occur. Rather, hybridization can occur when the 5' nucleotide sequence of one oligonucleotide has at least 80% (e.g., at least 85%, 90%, 95%, 99%, or 100%) sequence identity to the complement of the 5' nucleotide sequence of the other oligonucleotide. Hybridization of the 5' nucleotide sequences can be detected based on the level of fluorescence at the annealing temperature of a polymerase chain reaction (PCR) cycle, i.e., when the two oligonucleotides hybridize to each other under the annealing temperature, fluorescence resonance energy transfer (FRET) occurs and fluorescence is quenched. If hybridization does not occur, fluorescence is generated.

The percent identity of a nucleic acid sequence can be determined as follows. First, a nucleic acid sequence is compared to a target nucleic acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast"), the U.S. government's National Center for Biotechnology Information web site (World Wide Web at "ncbi" dot "nlm" dot "nih" dot "gov"), or the State University of New York at Old Westbury Library (QH 497.m6714). Instructions explaining how to use the Bl2seq program can be found in the readme file accompanying BLASTZ.

Bl2seq performs a comparison between two sequences using the BLASTN algorithm. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to –1; -r is set to 2; and all other options are left at their default settings. For example, the following command can be used to generate an output file containing a comparison between two sequences: C:\Bl2seq -i c:\seq1.txt -j c:\seq2.txt -p blastn -o c:\output.txt -q -1 -r 2. If the first nucleic acid sequence shares homology with any portion of the second nucleic acid sequence, then the designated output file will present those regions of homology as aligned sequences. If the first nucleic acid sequence does not share homology with any portion of the second nucleic acid sequence, then the designated output file will not present aligned sequences.

Once aligned, a length is determined by counting the number of consecutive nucleotides from the first nucleic acid sequence presented in alignment with sequence from the second nucleic acid sequence. A matched position is any position where an identical nucleotide is presented in both the target and mammalian sequence. Gaps presented in the first sequence are not counted since gaps are not nucleotides or amino acid residues. Likewise, gaps presented in the second sequence are not counted.

The percent identity over a determined length is determined by counting the number of matched positions over that length and dividing that number by the length followed by multiplying the resulting value by 100. For example, if (1) a 300 amino acid target sequence is compared to a reference sequence, (2) the Bl2seq program presents 200 consecutive amino acids from the target sequence aligned with a region of the reference sequence, and (3) the number of matches over those 200 aligned amino acids is 180, then that 300 amino acid target sequence contains an amino acid segment that has a length of 200 and a percent identity over that length of 90 (i.e., (180÷200)×100=90).

It is noted that the percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. It is also noted that the length value will always be an integer.

The 3' nucleotide sequences of the oligonucleotides of the invention have at least 80% (e.g., at least 85%, 90%, 95%, 99%, or 100%) sequence identity to different portions of a target nucleic acid such that a specific region of a target nucleic acid can be amplified (i.e., replicated such that multiple copies are produced) when the pair of oligonucleotide primers is used in the same PCR reaction. The 3' nucleotide sequence of one oligonucleotide has at least 80% sequence identity to the sense strand of the specific region of the target nucleic acid to be amplified while the other oligonucleotide has at least 80% sequence identity to the antisense strand of the specific region of the target nucleic acid. Typically, the 3' nucleotide sequences are 5 to 45 nucleotides in length.

In certain embodiments, the 3' nucleotide sequence of one or more of the oligonucleotides can comprise a portion of a vancomycin-resistant gene, such as the vanA gene from *Enterococcus faecium*. In certain embodiments, the 3' nucleotide sequence of one of the oligonucleotides comprises the nucleotide sequence set forth herein in SEQ ID NO:1 or SEQ ID NO:2, as shown in Table 1. In certain embodiments, the 3' nucleotide sequence of a first oligonucleotide can comprises the nucleotide sequence set forth in SEQ ID NO:1 and the 3' nucleotide sequence of a second oligonucleotide can comprises the nucleotide sequence set forth in SEQ ID NO:2.

TABLE 1

Nucleotide sequences of vanA oligonucleotides.

| SEQ ID NO: 1 | 5' TTGTGCGGTATTGGGAAACAGTG 3' |
|---|---|
| SEQ ID NO: 2 | 5' CCGGCTCGACTTCCTGATGAATA 3' |

An oligonucleotide consisting of the nucleotide sequence set forth in SEQ ID NO:1 can hybridize to a vanA nucleic acid target and corresponds to nucleotides 590-611 of GenBank Accession No. EF206285 (designated herein as SEQ ID NO:3), which describes a vanA partial gene sequence from *Enterococcus faecium*. An oligonucleotide consisting of the nucleotide sequence set forth in SEQ ID NO:2 can hybridize to a vanA nucleic acid target and corresponds to the reverse complement of nucleotides 667-689 of SEQ ID NO:3).

An oligonucleotide comprising a 3' nucleotide sequence as set forth in SEQ ID NO:1, or an oligonucleotide comprising a 3' nucleotide sequence as set forth in SEQ ID NO:2, or a mixture of oligonucleotides wherein a first oligonucleotide comprises the 3' nucleotide sequence as set forth in SEQ ID NO:1 and a second oligonucleotide comprises the 3' nucleotide sequence as set forth in SEQ ID NO:2 can be used in a method to detect a target nucleic acid according to the present disclosure. An oligonucleotide consisting essentially of a 3' nucleotide sequence as set forth in SEQ ID NO:1, or an oligonucleotide consisting essentially of a 3' nucleotide sequence as set forth in SEQ ID NO:2, or a mixture of oligonucleotides wherein a first oligonucleotide consists essentially of the 3' nucleotide sequence as set forth in SEQ ID NO:1 and a second oligonucleotide consists essentially of the 3' nucleotide sequence as set forth in SEQ ID NO:2 can be used in a method to detect a target nucleic acid according to the present disclosure.

TABLE 2

Partial vanA nucleotide sequence from *E. faecium* as set forth in GenBank Accession No. EF206285.

| SEQ ID NO: 3 | 1 ggtaaaatct gcaatagaga tagccgctaa cattaataaa |
|---|---|
| | 41 gaaaaatacg agccgttata cattggaatt acgaaatctg |

TABLE 2-continued

Partial vanA nucleotide sequence from *E. faecium* as set forth in GenBank Accession No. EF206285.

```
 81  gtgtatggaa aatgtgcgaa aaaccttgcg cggaatggga
121  aaacgacaat tgctattcag ctgtactctc gccggataaa
161  aaaatgcacg gattacttgt taaaaagaac catgaatatg
201  aaatcaacca tgttgatgta gcattttcag ctttgcatgg
241  caagtcaggt gaagatggat ccatacaagg tctgtttgaa
281  ttgtccggta tcccttttgt aggctgcgat attcaaagct
321  cagcaatttg tatggacaaa tcgttgacat acatcgttgc
361  gaaaaatgct gggatagcta ctcccgcctt ttgggttatt
401  aataaagatg ataggccggt ggcagctacg tttacctatc
441  ctgtttttgt taagccggcg cgttcaggct catccttcgg
481  tgtgaaaaaa gtcaatagcg cggacgaatt ggactacgca
521  attgaatcgg caagacaata tgacagcaaa atcttaattg
561  agcaggctgt ttcgggctgt gaggtcggtt gtgcggtatt
601  gggaaacagt gccgcgttag ttgttggcga ggtggaccaa
641  atcaggctgc agtacggaat ctttcgtatt catcaggaag
681  tcgagccgga aaaaggctct gaaaacgcag ttataaccgt
721  tcccgcagac ctttcagcag aggagcgagg acggatacag
761  gaaacggcaa aaaaaatata taaagcgctc ggctgtagag
801  gtctagcccg t
```

An oligonucleotide consisting of the nucleotide sequence set forth in SEQ ID NO:4 can hybridize to SEQ ID NO:3. An oligonucleotide consisting of the nucleotide sequence set forth in SEQ ID NO:5 can hybridize to SEQ ID NO:3.

An oligonucleotide comprising the nucleotide sequence as set forth in SEQ ID NO:4, or an oligonucleotide comprising the nucleotide sequence as set forth in SEQ ID NO:5, or a mixture of oligonucleotides wherein a first oligonucleotide comprises the nucleotide sequence as set forth in SEQ ID NO:4 and a second oligonucleotide comprises the nucleotide sequence as set forth in SEQ ID NO:5 can be used in a method to detect a target nucleic acid according to the present disclosure. An oligonucleotide consisting essentially of the nucleotide sequence as set forth in SEQ ID NO:4, or an oligonucleotide consisting essentially of the nucleotide sequence as set forth in SEQ ID NO:5, or a mixture of oligonucleotides wherein a first oligonucleotide consists essentially of the nucleotide sequence as set forth in SEQ ID NO:4 and a second oligonucleotide consists essentially of the nucleotide sequence as set forth in SEQ ID NO:5 can be used in a method to detect a target nucleic acid according to the present disclosure.

TABLE 3

Nucleotide sequences of oligonucleotides that hybridize to the vanA gene.

| SEQ ID NO: 4 | 5' CACCACCACCACCTTGTGCGGTATTG GGAAACAGTG 3' |
|---|---|

TABLE 3-continued

Nucleotide sequences of oligonucleotides that hybridize to the vanA gene.

| SEQ ID NO: 5 | 5' GGTGGTGGTGGTGCCGGCTCGACTTC CTGATGAATA 3' |
|---|---|

Figure 1B:
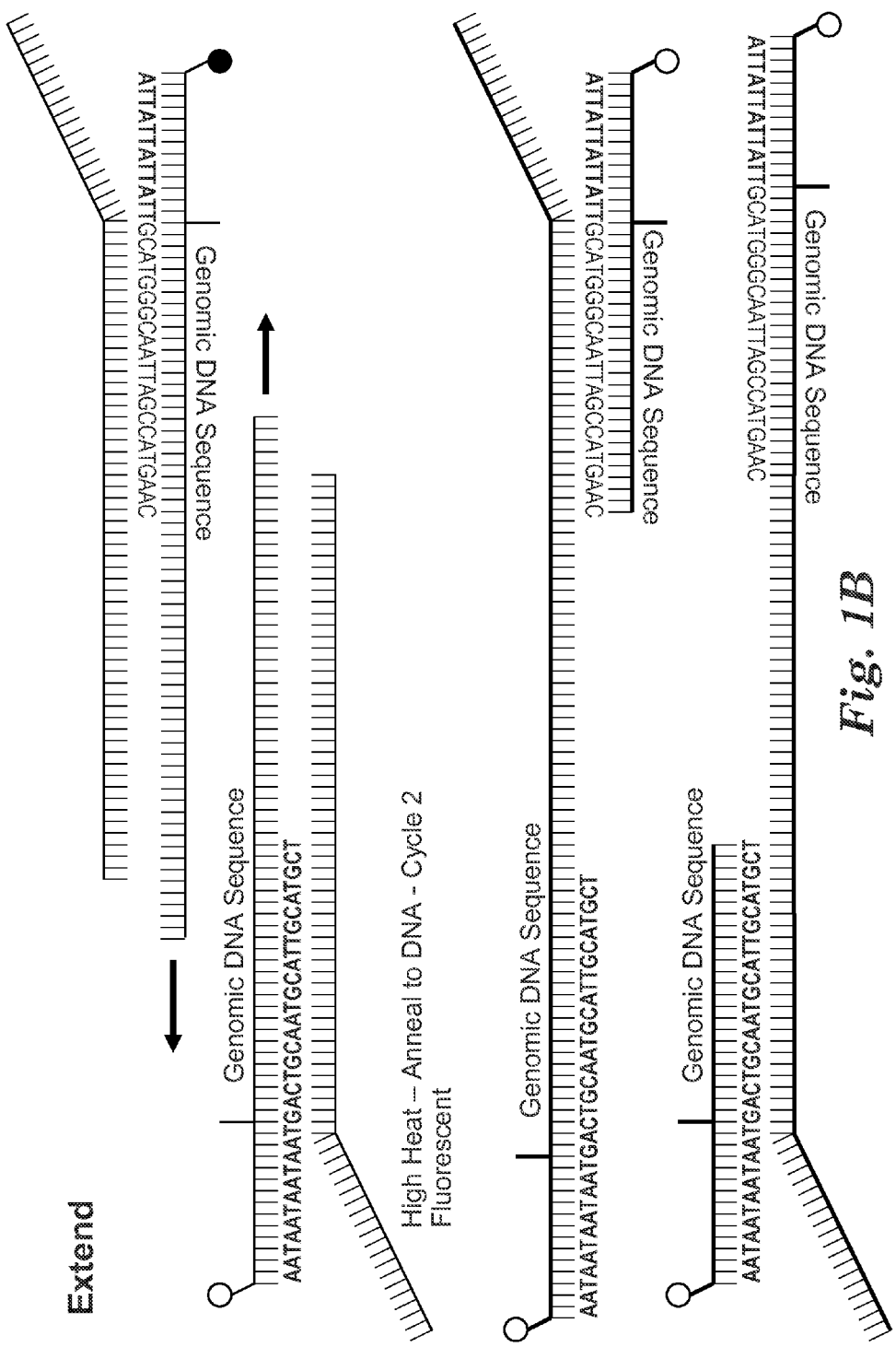

The 5' nucleotide sequences of the oligonucleotides (e.g., oligonucleotides comprising or consisting essentially of any one of the nucleotide sequences set forth in SEQ ID NOS: 4, 5, 6, or 7) are designed such that the annealing temperature of the 5' nucleotide sequences to each other is lower than the annealing temperature between the 3' nucleotides sequences and their targets. For example, the annealing temperature of the 5' nucleotide sequences can be 5 to 20° C. (e.g., 6 to 18° C., 7 to 17° C., 8 to 14° C., or 9 to 11° C.) lower than the annealing temperature of the 3' nucleotide sequences to their targets. This allows the 3' nucleotide sequence of each oligonucleotide to anneal to its target before the oligonucleotides anneal to each other (i.e., as a primer dimer). See, FIG. 1A-1C. A greater difference between the annealing temperature of the 5' nucleotide sequences to each other and the annealing temperature of the 3' nucleotide sequences with their target sequences, allows the reaction to be biased towards the annealing of the oligonucleotides to their targets before reaching the final annealing temperature at which the oligonucleotides can anneal to each other and form primer dimers Annealing temperature can be determined empirically or by subtracting 5 to 10° C. from the calculated melting temperature (Tm) of an oligonucleotide. The Tm value on an oligonucleotide depends on the length of the sequence, guanine+cytosine content of the sequence, and the type and concentration of present cations, particularly sodium ions (Na+), and can be calculated by the method of SantaLucia (Proc Natl Acad Sci USA (1998) 95: 1460-5).

In certain embodiments, the 5' nucleotide sequence of the oligonucleotide can comprise the nucleotide sequence set forth in SEQ ID NO:6 or SEQ ID NO:7.

TABLE 4

| Oligonucleotide 5' nucleotide sequences | |
|---|---|
| SEQ ID NO: 6 | 5' CACCACCACCACC 3' |
| SEQ ID NO: 7 | 5' GGTGGTGGTGGTG 3' |

An oligonucleotide comprising the 5' nucleotide sequence as set forth in SEQ ID NO:6, or an oligonucleotide comprising the 5' nucleotide sequence as set forth in SEQ ID NO:7, or a mixture of oligonucleotides wherein a first oligonucleotide comprises the 5' nucleotide sequence as set forth in SEQ ID NO:6 and a second oligonucleotide comprises the 5' nucleotide sequence as set forth in SEQ ID NO:7 can be used in a method to detect a target nucleic acid according to the present disclosure. An oligonucleotide consisting essentially of the 5' nucleotide sequence as set forth in SEQ ID NO:6, or an oligonucleotide consisting essentially of the 5' nucleotide sequence as set forth in SEQ ID NO:7, or a mixture of oligonucleotides wherein a first oligonucleotide consists essentially of the 5' nucleotide sequence as set forth in SEQ ID NO:6 and a second oligonucleotide consists essentially of the 5' nucleotide sequence as set forth in SEQ ID NO:7 can be used in a method to detect a target nucleic acid according to the present disclosure.

The 5' nucleotide sequence of each oligonucleotide (e.g., oligonucleotides comprising or consisting essentially of any one of the nucleotide sequences set forth in SEQ ID NOS: 4, 5, 6, or 7) is labeled with a fluorescent donor moiety or an acceptor moiety. The 3' nucleotide sequence of each oligonucleotide is not labeled with a fluorescent donor moiety or an acceptor moiety that is compatible with a fluorescent moiety or acceptor moiety attached to any oligonucleotide within the set. In many embodiments, the 5' nucleotide sequence is labeled at its 5' end, i.e., the 5' terminal nucleotide is labeled. A wide variety of fluorescent donors is known in the literature, including, for example, xanthene dyes, such as fluorescein or rhodamine dyes, including 5-carboxyfluorescein (FAM), 6-carboxyfluorescein (6-FAM), hexachlorofluorescein (HEX), 2'7'-dimethoxy-4'5'-dichloro-6-carboxyfluorescein (JOE), tetrachlorofluorescein (TET), fluorinated analogs of fluoresceins (e.g., Oregon Green3), 6-carboxyrhodamine (R6G), N,N,N,N'-tetramethyl-6-carboxyrhodamine (TAMRA), 6-carboxy-X-rhodamine (ROX). Suitable fluorescent donors also include the naphthylamine dyes that have an amino group in the alpha or beta position. Non-limiting examples of naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other fluorescent donors include coumarins, such as 3-phenyl-7-isocyanatocoumarin; acridines, such as 9-isothiocyanatoacridine and acridine orange; N-(p-(2-benzoxazolyl) phenyl)maleimide; cyanines, such as indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); lH,5H,1 1H,1 5H-Xantheno [2,3,4-ij:5,6, 7-i'j']diquinolizin-18-ium, 9-[2 (or 4)-[[[6-[2,5-dioxo-1-pyrrolidinyl)oxy]-6-oxohexyl]amino]sulfonyl]-4 (or 2)-sulfophenyl]-2,3,6,7,12,13,16,17-octahydro-inner salt (TR or Texas Red); BODIPY dyes; benzoxadiazoles; stilbenes; pyrenes; and the like.

The 5' acceptor moiety must be compatible with the 5' donor fluorescent moiety. As used herein, a "compatible acceptor" is a molecule whose absorbance spectrum overlaps with the emission spectrum of the donor. Acceptor moieties can be quenchers, i.e., a non-fluorescent molecule that causes the donor moiety to decrease its fluorescence emission intensity, or a fluorescent molecule that accepts the energy non-radiatively from the donor and re-emits the energy with the acceptor's characteristic emission spectrum. See, Epstein et al. (2002) *Analytica Chimica Acta*, 469:3-36.

Non-limiting examples of acceptor moieties include TAMRA, Dabcyl (4-(dimethylaminoazo)benzene-4-carboxylic acid), a Black Hole Quencher® such as BHQ®-1 (maximally absorbs light in the wavelength range of 500-550 nm), BHQ®-2, BHQ®-3 (maximally absorbs light in the wavelength range of 650-700 nm), Iowa Black3 FQ (maximally absorbs light between 420 and 700 nm (e.g., between 420 and 620 nm), LC™-Red 640, LC™-Red 705, Cy5, Cy5.5 (maximally absorbs light between 500 and 705 nm), Lissamine rhodamine B sulfonyl chloride, tetramethyl rhodamine isothiocyanate, rhodamine×isothiocyanate, erythrosine isothiocyanate, fluorescein, diethylenetriamine pentaacetate or other chelates of Lanthanide ions (e.g., Europium, or Terbium). For example, 6-FAM, Rhodamine Green, Oregon Green, HEX, JOE, TET, or Cy3 can be used as a fluorescent donor and Iowa Black3 FQ can be used as an acceptor. See, for example, U.S. Patent Application Publication No. 20060263816 for methods of synthesizing dark quenchers and linking dark quenchers to oligonucleotides. Donor and acceptor moieties can be obtained, for example, from Molecular Probes (Junction City, Oreg.), Integrated DNA Technologies, Inc. (Coralville, Iowa), or Sigma Chemical Co. (St. Louis, Mo.).

Upon hybridization of the 5' labeled oligonucleotides to each other, the fluorescent donor and compatible acceptor moieties must be in close proximity such that FRET can occur. FRET technology (see, for example, U.S. Pat. Nos. 4,996,143, 5,565,322, 5,849,489, and 6,162,603) is based on a concept that when a donor and a compatible acceptor moiety are positioned within the Förster distance of each other, energy transfer takes place between the two moieties that can be visualized or otherwise detected and/or quantitated. Förster distance refers to the distance at which resonance energy transfer between compatible FRET pairs drops to 50% and is typically between 10 and 100 Å. Thus, upon hybridization of the oligonucleotides to each other, the 5' donor and 5' acceptor moieties of each oligonucleotide can be up to 23 (e.g., 1, 2, 3, 4, 5, 6, 7, 8, 9, 10, 11, 12, 13, 14, 15, 16, 17, 18, 19, 20, 21, 22, or 23) nucleotides apart. Preferably, the 5' labels are within 1 to 20 (e.g., 3 to 20, 4 to 19, 6 to 18, 8 to 15, or 11 to 14) nucleotides of each other. When the acceptor moiety is a quencher, decreased fluorescence emission intensity will be observed upon hybridization of the two oligonucleotides to each other. It is particularly useful to have a reduction in at least 50%, 60%, 70%, 80%, 90%, 95%, or 98% of the fluorescence of the donor relative to the fluorescence of the fluorescent molecule in the absence of quenching. If the acceptor moiety is another fluorescent moiety, fluorescence will be observed at the acceptor's characteristic emission spectrum, while donor fluorescence decreases.

Methods for synthesizing oligonucleotides are known. Typically, an automated DNA synthesizer, such as available from Applied Biosystems (Foster City, Calif.), is used. Once an oligonucleotide is synthesized and any protecting groups are removed, the oligonucleotide can be purified (e.g., by extraction and gel purification or ion-exchange high performance liquid chromatography (HPLC)) and the concentration of the oligonucleotide can be determined (e.g., by measuring optical density at 260 nm in a spectrophotometer).

The oligonucleotides can be labeled with donor or acceptor moieties during synthesis of the oligonucleotide or the donor or acceptor moieties can be attached after synthesis. A linker molecule can be used to attach a donor or acceptor moiety to an oligonucleotide using techniques known in the art. See, for example, The Handbook A Guide to Fluorescent Probes and Labeling Technologies from Molecular Probes (at probes.invitrogen.com/handbook). Linkers frequently used to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Methods of Detecting Nucleic Acid

The methods disclosed herein can be used for detecting nucleic acids from any organism, including any microorganism, plant, or animal (e.g., a mammal such as a mouse, a rat, a cat, a dog, a horse, a cow, a non-human primate such as a cynomolgus monkey, or a human). As such, the methods can be used to diagnose the presence of an infectious disease agent (e.g., a microorganism that causes human disease) in a biological sample (e.g., a food product or a blood or tissue sample from a human).

Microorganisms of particular interest include prokaryotic and eukaryotic organisms, particularly Gram positive bacteria, Gram negative bacteria, fungi, protozoa, mycoplasma, yeast, viruses, and lipid-enveloped viruses. Typically, Gram positive or Gram negative bacteria can be identified by detecting the presence of a cell-wall component characteristic of the bacteria, such as a nucleic acid encoding a cell-wall protein. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Listeria* spp., *Vibrio* spp., *Corynebacteria* spp. as well as herpes virus, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis, Streptococcus pneumoniae, S. agalactiae, S. pyogenes, Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracis, Pseudomonas aeruginosa, Escherichia coli, Aspergillus niger, A. fumigatus, A. clavatus, Fusarium solani, F. oxysporum, F. chlamydosporum, Listeria monocytogenes, Listeria ivanovii, Vibrio cholera, V. parahaemolyticus, Salmonella choleraesuis, S. typhi, S. typhimurium, Candida albicans, C. glabrata, C. krusei, Enterobacter sakazakii, E. coli* O157 and multiple drug resistant Gram negative rods (MDR). Typically, antibiotic resistant microbes can be detected by the presence of a nucleic acid encoding an internal cell component, such as a membrane protein, transport protein, enzyme, etc., that is responsible for antibiotic resistance.

The presence or absence of a target nucleic acid in a biological sample can be detected by contacting the biological sample with a pair of oligonucleotides as described above to produce a fluorescently labeled amplicon if the target nucleic acid is present in the sample. As used herein, "amplicon" refers to a double-stranded amplification product that typically is from 30 and 500 nucleotides in length (e.g., from 30-300, 30-200, 30-150, or 50-150 nucleotides in length). Within the fluorescently labeled amplicon, the 5' nucleotide sequence of the sense strand has at least 80% (e.g., at least 85%, 90%, 95%, 99%, or 100%) sequence identity to the complement of the 5' nucleotide sequence of the antisense strand. The terms "sense strand" and "antisense strand" are used herein to designate each strand of the double-stranded nucleic acid molecule, and are not limited to coding regions of the nucleic acid. The 5' nucleotide sequences are 5 to 23 nucleotides in length, beginning at the 5' end of each strand of the amplicon. Furthermore, the 5' nucleotide sequence of one strand is labeled with a fluorescent moiety and the 5' nucleotide sequence of the other strand is labeled with a compatible acceptor moiety. In one embodiment, the 5' terminal nucleotide of each strand is labeled. See, for example, FIG. 1C.

The contacting step takes place under PCR (e.g., real-time PCR) conditions such that the target nucleic acid, if present, can be amplified to produce a fluorescently labeled amplicon. Typically, amplicons produced under real-time PCR conditions range from 30-200 (e.g., 30-150 or 50-150) nucleotides in length. In the methods described herein, amplifying a nucleic acid molecule includes denaturing the template nucleic acid, annealing the oligonucleotide primers to the target nucleic acid and to each other by reducing the temperature gradually until a final annealing temperature is reached that is below the melting temperature of the 5' nucleotide sequence of the primers, and enzymatically elongating from the primers to generate a fluorescently labeled amplicon. As discussed above, the 3' nucleotide sequences of the oligonucleotide primers anneal to their targets at a temperature that is higher than the annealing temperature of the 5' nucleotide sequences of the oligonucleotide primers to each other. The formation of primer dimers does not contribute to background fluorescence as quenching occurs and the primer dimers cannot be extended by the polymerase. As such, primer dimer formation does not interfere with the reaction.

Amplification typically requires the presence of deoxyribonucleoside triphosphates (dNTPs), a DNA polymerase enzyme (e.g., Platinum® Taq) and an appropriate buffer and/or co-factors for optimal activity of the polymerase enzyme. PCR conditions typically are defined by the concentration of salts (e.g., $MgCl_2$ and KCl) in the reaction buffer, and by the temperatures utilized for melting, annealing, and extension. Specific concentrations or amounts of oligonucleotide primers, target nucleic acid, dNTPs, and DNA polymerase also may be set out. For example, PCR conditions with a buffer containing 1.5 to 2.5 mM $MgCl_2$, and melting, annealing, and extension temperatures of 94-95° C., 35-65° C. (e.g., 42-50° C.), and 60-72° C., respectively, can be particularly useful. In some embodiments, commercially available mixes that contain the appropriate concentration of buffer, salt, dNTPs, and DNA polymerase (e.g., GeneAmp® Fast PCR Master Mix (2×) from Applied Biosystems) can be used. Denaturation, annealing, and extension each may be carried out, for example, for 15-45 seconds (e.g., 30 seconds) per cycle, with a total of 25 to 50 cycles (e.g., 45 cycles). An initial denaturation step (e.g., 94-95° C. for 1 to 2 minutes) and/or a final elongation step (e.g., 60-72° C. for 1 to 10 minutes) also may be useful. For example, denaturation can be carried out at 95° C. for 1 minute followed by 45 cycles of denaturation at 95° C. for 15 seconds, annealing at 45° C. for 30 seconds, and extension at 60° C. for 30 seconds. Temperature can be reduced or increased as needed between the denaturation, annealing, and extension steps at 5-30° C. (e.g., 20° C.) per second.

A single PCR reaction mixture may contain one set of oligonucleotide primers. One set of primers is a pair of, i.e., two, oligonucleotides. Alternatively, a single reaction mixture may contain a plurality of oligonucleotide primer sets, in which case multiple amplicons can be generated. Each set of primers can amplify, for example, a coding region or a portion thereof (e.g., a full-length coding sequence, one exon, or a portion of an exon) or a non-coding region or a portion thereof (e.g., a promoter or an intron, or portions thereof). In embodiments in which two or more sets of oligonucleotide primers are used, the 3' nucleotide sequences of each set of oligonucleotides can be designed such that amplicons from two or more target nucleic acids (e.g., to detect one or more of a group of microorganisms), or two or more regions of the same target nucleic acid (e.g., to maximize the inclusivity of a test for microorganisms that have genetic variation), are produced The 5' nucleotide sequences of the primer pairs can have the same or different nucleotide sequences.

Fluorescence of the amplicon can be detected, and in some embodiments, quantitated, using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range. Fluorescence detection can be performed after the final annealing temperature has been reached and the oligonucleotides have annealed to each other. The cycle number at which FRET is detectable (i.e., Ct value) can be correlated with the amount of target nucleic acid in a biological sample.

More typically, multiple contacting and detecting steps take place within a thermocycler device such as the LIGHT-CYCLER (Roche) (University of Utah Research Foundation, International Publication Nos. WO 97/46707, WO 97/46714, and WO 97/46712), Mx3005P Real-Time PCR System (Stratagene, La Jolla, Calif.), or amplification devices available from Bio-Rad. It may be preferred that the present invention is practiced in connection with a microfluidic device. "Microfluidic" refers to a device with one or more fluid passages, chambers, or conduits that have at least one internal cross-sectional dimension, e.g., depth, width, length, diameter, etc., that is less than 500 μm, and typically between 0.1 μm and 500 μm. Typically, a microfluidic device includes a plurality of chambers (e.g., amplification reaction chambers, loading chambers, and the like), each of the chambers defining a volume for containing a sample. Some examples of potentially suitable microfluidic devices are described in U.S. Pat. Nos. 6,627,159 (Bedingham et al.); 6,720,187 (Bedingham et al.); 6,734,401 (Bedingham et al.); 6,814,935 (Harms et al.); 6,987,253 (Bedingham et al.); 7,026,168 (Bedingham et al.); 7,164,107 (Bedingham et al.), and 7,192,560 (Parthasarathy et al.). It is understood that the present invention is not limited by the device used to amplify and detect the amplicon.

In some embodiments, the methods of the invention can include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel typically are performed for accuracy in a diagnostic laboratory handling clinical samples.

Control samples also can be cycled within each round of PCR (e.g., each thermocycler run). Positive control samples can amplify a nucleic acid control template (e.g., from a plasmid) using, for example, control oligonucleotide primers. Such a plasmid control can be amplified internally (e.g., within the biological sample) or in a separate sample run side-by-side with the test samples. Each thermocycler run also can include a negative control that, for example, lacks target nucleic acid. Such controls are indicators of the success or failure of the amplification and/or FRET reaction. Therefore, control reactions can readily determine, for example, the ability of primers to anneal with sequence-specificity and to initiate elongation, and for FRET to occur.

Articles of Manufacture

Oligonucleotides of the invention can be combined with packaging material and sold as a kit for detecting nucleic acids from biological samples. For example, a kit can include oligonucleotides for detecting a particular microorganism (e.g., *Staphylococcus aureus* (including MRSA), *S. epidermidis*, *Streptococcus pneumoniae*, *S. agalactiae*, *S. pyogenes*, *Enterococcus faecalis*, VRE, VRSA, VISA, *Bacillus anthracis*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Listeria monocytogenes*, *Listeria ivanovii*, *Vibrio cholera*, *V. parahaemolyticus*, *Salmonella choleraesuis*, *S. typhi*, *S. typhimurium*, *Candida albicans*, *C. glabrata*, *C. krusei*, *Enterobacter sakazakii*, *E. coli* O157 and MDR. Components and methods for producing articles of manufactures are well known. The articles of manufacture may combine two or more oligonucleotides as described herein. Furthermore, an article of manufacture can include one or more additional sets of oligonucleotide primers (e.g., 3, 4, 5, or 6 primer pairs), such that multiple nucleic acid products can be generated.

Articles of manufacture of the invention also can include one or more donor fluorescent moieties or acceptor moieties for labeling the oligonucleotides, or alternatively, the oligonucleotides supplied with the kit can be labeled. For example, an article of manufacture may include a donor fluorescent moiety for labeling one of the oligonucleotides and a compatible quencher moiety for labeling the other oligonucleotide. Examples of suitable FRET donor fluorescent moieties and compatible acceptor moieties are provided above.

Articles of manufacture also may include reagents for carrying out the methods disclosed herein (e.g., buffers, a DNA polymerase, $MgCl_2$, KCl, $MgSO_4$, dNTPs, co-factors, control nucleic acids, agents to prevent contamination, or other useful reagents for performing PCR reactions). Such reagents may be specific for one of the commercially available instruments described herein. Instructions describing how the oligonucleotides can be used for detecting nucleic acids also may be included in such kits.

In some embodiments, an article of manufacture can include a reaction mixture for fluorescence-based monitoring of PCR. The reaction mixture can include a set of oligonucleotides as discussed herein and reagents for performing PCR reactions. For example, a DNA polymerase, dNTPs, and $MgCl_2$ or KCl can be included in a reaction mixture. Such an article of manufacture further can include instructions describing how the reaction mixture can be used for detecting nucleic acids.

The invention will be further described in the following examples, which do not limit the scope of the invention described in the claims.

EXAMPLE

In this example, a pair of 5' labeled primers was used to amplify and detect the vanA gene of vancomycin resistant *Enterococcus faecium* (ATCC 700221, Manassas Va.) (VRE). *E. faecium* was streaked onto blood agar media and incubated at 37° C. for 20 hours. After the incubation, a cell suspension was prepared by diluting a sample of the fresh growth in TE buffer (10 mM Tris HCl, 1 mM EDTA, pH 8.0) to a McFarland standard of 0.5, which equates to approximately $1 \times 10^8$ CFU/mL. *E. faecium* DNA was extracted and isolated from 100 TL of the cell suspension using the MagNA Pure LC DNA Isolation Kit III (Bacteria, Fungi) kit (instrument and reagents obtained from Roche, Indianapolis, Ind.) per manufacturer's instructions.

The following primers were synthesized by Integrated DNA Technologies (Coralville, Iowa). The vanA forward primer sequence, 5' CACCACCACCACCTTGTGCGGTAT-TGGGAAACAGTG 3' (SEQ ID NO: 4), was labeled by 6-carboxy-4',5'-dichloro-2',7'-dimethoxyfluorescein (JOE) (Integrated DNA Technologies, Coralville, Iowa) at the 5' position. The vanA reverse primer sequence, 5' GGTGGTG-GTGGTGCCGGCTCGACTTCCTGATGAATA 3'(SEQ ID NO:5) was labeled by Iowa Black3 FQ (Integrated DNA Technologies, Coralville, Iowa) at the 5' position.

Purified *E. faecium* DNA was subjected to real-time PCR amplification, which was performed in duplicate using 3.5 µL of each sample with varying concentrations of probes. In particular, PCR amplification was performed in a total volume of 10 µL containing 3.5 µL of sample and 6.5 µL of the following mixture: two primers of varying initial concentrations—2 µM and 4 µM (0.5 µL of each), and GeneAmp® Fast PCR Master Mix (5.5 µL of 2×, Applied Biosystems, Foster City, Calif.). Amplification was performed on the Stratagene Mx3005P Real-Time PCR System (Stratagene) with the following protocol: an initial denaturation at 95° C. for 60 seconds followed by 45 PCR cycles of 95° C. for 15 seconds (20° C./s slope), 45° C. for 30 seconds (20° C./s slope, single acquisition), and 60° C. for 30 seconds (20° C./s slope). Results were analyzed using the software provided with the Stratagene Mx3005P Real Time PCR System. The probes successfully amplified the vanA gene under the conditions presented in this example as shown in Table 5. The Ct value in Table 5 refers to the cycle number at which the increase in fluorescence is exponential and crosses the threshold.

TABLE 5

| Real-Time PCR Amplification of vanA from VRE | | |
|---|---|---|
| Sample | Ct | |
| 2 µM Forward / 2 µM Reverse | 20.14 | 19.87 |
| 2 µM Forward / 4 µM Reverse | 19.5 | 19.2 |
| 4 µM Forward / 2 µM Reverse | 19.36 | 19.28 |
| 4 µM Forward / 4 µM Reverse | 19.07 | 18.86 |
| No Template Control: | | |
| 2 µM Forward / 2 µM Reverse | 37.37 | 36.72 |

These results show that the vanA gene was successfully amplified and detected using the 5' labeled primers having the nucleotide sequences set forth in SEQ ID NO:4 and SEQ ID NO:5. Analysis of reaction products from each of the reactions on a 2.2% Agarose Flash Gel (Lonza, Basel, Switzerland) displayed products for each sample except the No Template Controls.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of a target nucleic acid in a biological sample, said method comprising:
- (a) contacting said biological sample with a set of oligonucleotides to produce a fluorescently labeled amplicon if said target nucleic acid is present in said sample, said set of oligonucleotides under reaction conditions comprising:
  - i) a first oligonucleotide comprising a 5' and 3' nucleotide sequence, wherein said 5' nucleotide sequence is 5-23 nucleotides in length beginning at the 5' end of said first oligonucleotide, wherein said 3' sequence is complementary to a first portion of said target nucleic acid, and wherein a fluorescent moiety is attached in the 5' nucleotide sequence of said first oligonucleotide; and
  - ii) a second oligonucleotide comprising a 5' and 3' nucleotide sequence, wherein said 5' nucleotide sequence is 5-23 nucleotides in length beginning at the 5' end of said second oligonucleotide, wherein said 3' nucleotide sequence is complementary to a second portion of said target nucleic acid, and wherein an acceptor moiety is attached in the 5' nucleotide sequence of said second oligonucleotide; wherein said 5' nucleotide sequence of said first oligonucleotide is at least 80% identical to the complement of said 5' nucleotide sequence of said second oligonucleotide, and wherein the 3' nucleotide sequence of each of said oligonucleotide is not labeled with a fluorescent moiety or an acceptor moiety that is compatible with said fluorescent moiety attached to said first oligonucleotide or said acceptor moiety attached to said second oligonucleotide; and
- (b) detecting fluorescence of said amplicon.

2. The method of claim 1, wherein said 3' sequence of said first oligonucleotide is at least 80% identical to said first portion of said target nucleic acid, wherein said 3' nucleotide sequence of said second oligonucleotide is at least 80% identical to said second portion of said target nucleic acid, and wherein said first oligonucleotide or second oligonucleotide comprises a modified base.

3. The method of claim 1, wherein said contacting and detecting steps take place under real-time PCR conditions.

4. The method of claim 3, wherein said detecting step comprises quantitating the amount of fluorescence.

* * * * *

UNITED STATES PATENT AND TRADEMARK OFFICE
CERTIFICATE OF CORRECTION

PATENT NO. : 8,652,812 B2  
APPLICATION NO. : 13/681574  
DATED : February 18, 2014  
INVENTOR(S) : Jesse D. Miller Page 1 of 1

It is certified that error appears in the above-identified patent and that said Letters Patent is hereby corrected as shown below:

In the Specification

Column 8
Line 65, "dimers" should read --dimers.--.

Column 9
Line 53, "N,N,N,N'" should read --N, N, N, N'--.
Line 67, "1H,5H,1 1H, 1 5H" should read --1H, 5H, 11H, 15H--.

Column 15
Line 39, "uLof" should read --µL of--.

Signed and Sealed this  
Twenty-eighth Day of April, 2015

Michelle K. Lee  
*Director of the United States Patent and Trademark Office*

SEQUENCE LISTING

<160> NUMBER OF SEQ ID NOS: 7

<210> SEQ ID NO 1
<211> LENGTH: 23
<212> TYPE: DNA
<213> ORGANISM: Enterococcus faecium

<400> SEQUENCE: 1
ttgtgcggta ttgggaaaca gtg                    23

<210> SEQ ID NO 2
<211> LENGTH: 23
<212> TYPE: DNA
<213> ORGANISM: Enterococcus faecium

<400> SEQUENCE: 2
ccggctcgac ttcctgatga ata                    23

<210> SEQ ID NO 3
<211> LENGTH: 811
<212> TYPE: DNA
<213> ORGANISM: Enterococcus faecium -continued

```
<400> SEQUENCE: 3
ggtaaaatct gcaatagaga tagccgctaa cattaataaa gaaaaatacg agccgttata      60
cattggaatt acgaaatctg gtgtatggaa aatgtgcgaa aaaccttgcg cggaatggga     120
aaacgacaat tgctattcag ctgtactctc gccggataaa aaaatgcacg gattacttgt     180 taaaagaac catgaatatg aaatcaacca tgttgatgta gcattttcag ctttgcatgg      240
caagtcaggt gaagatggat ccatacaagg tctgtttgaa ttgtccggta tccctttttgt    300 aggctgcgat attcaaagct cagcaatttg tatggacaaa tcgttgacat acatcgttgc     360
gaaaaatgct gggatagcta ctcccgcctt ttgggttatt aataaagatg ataggccggt     420
ggcagctacg tttacctatc ctgttttttgt taagccggcg cgttcaggct catccttcgg    480
tgtgaaaaaa gtcaatagcg cggacgaatt ggactacgca attgaatcgg caagacaata    540
tgacagcaaa atcttaattg agcaggctgt ttcgggctgt gaggtcggtt gtgcggtatt    600
gggaaacagt gccgcgttag ttgttggcga ggtggaccaa atcaggctgc agtacggaat    660
ctttcgtatt catcaggaag tcgagccgga aaaaggctct gaaaacgcag ttataaccgt    720
tcccgcagac ctttcagcag aggagcgagg acggatacag gaaacggcaa aaaaaatata   780
taaagcgctc ggctgtagag gtctagcccg t                                    811

<210> SEQ ID NO 4
<211> LENGTH: 36
<212> TYPE: DNA
<213> ORGANISM: Artificial Sequence
<220> FEATURE:
<223> OTHER INFORMATION: Primer derived from E. faecium vanA gene

<400> SEQUENCE: 4
caccaccacc accttgtgcg gtattgggaa acagtg                                36

<210> SEQ ID NO 5
<211> LENGTH: 36
<212> TYPE: DNA
<213> ORGANISM: Artificial Sequence
<220> FEATURE:
<223> OTHER INFORMATION: Primer derived from E. faecium vanA gene

<400> SEQUENCE: 5
ggtggtggtg gtgccggctc gacttcctga tgaata                                36

<210> SEQ ID NO 6
<211> LENGTH: 13
<212> TYPE: DNA
<213> ORGANISM: Artificial Sequence
<220> FEATURE:
<223> OTHER INFORMATION: Synthetic oligonucleotide (I) for 3' sequence

<400> SEQUENCE: 6
caccaccacc acc                                                         13

<210> SEQ ID NO 7
<211> LENGTH: 13
<212> TYPE: DNA
<213> ORGANISM: Artificial Sequence
<220> FEATURE:
<223> OTHER INFORMATION: Synthetic oligonucleotide (II) for 3' sequence

<400> SEQUENCE: 7
ggtggtggtg gtg                                                         13
```